(12) United States Patent
Castino

(10) Patent No.: US 6,428,712 B1
(45) Date of Patent: Aug. 6, 2002

(54) GRAVITY DRIVEN LIQUID FILTRATION SYSTEM AND METHOD FOR FILTERING BIOLOGICAL LIQUID

(75) Inventor: Franco Castino, Sudbury, MA (US)

(73) Assignee: Hemasure, Inc., Marlborough, MA (US)

( * ) Notice: Subject to any disclaimer, the term of this patent is extended or adjusted under 35 U.S.C. 154(b) by 0 days.

(21) Appl. No.: 09/544,383

(22) Filed: Apr. 6, 2000

(51) Int. Cl.$^7$ ............................................. B01D 37/00
(52) U.S. Cl. ................... 210/800; 210/749; 210/767; 210/806
(58) Field of Search ............... 210/749, 767, 210/800, 806, 252, 258, 435; 435/2

(56) References Cited

U.S. PATENT DOCUMENTS

| | | | |
|---|---|---|---|
| 4,898,573 A | 2/1990 | Takenaka et al. | 604/6 |
| 4,997,577 A | 3/1991 | Stewart | 210/767 |
| 5,128,048 A | 7/1992 | Stewart et al. | 210/749 |
| 5,135,646 A | 8/1992 | Tanokura et al. | 210/109 |
| 5,180,504 A | 1/1993 | Johnson et al. | 210/767 |
| 5,451,321 A | 9/1995 | Matkovich | 210/641 |
| 5,470,488 A | 11/1995 | Matkovich et al. | 210/767 |
| 5,512,187 A | 4/1996 | Buchholz et al. | 210/767 |
| 5,527,472 A | 6/1996 | Bellotti et al. | 210/767 |
| 5,601,730 A | 2/1997 | Page et al. | 210/806 |
| 5,690,815 A | * 11/1997 | Krasnoff et al. | 210/97 |
| 5,776,338 A | 7/1998 | Mari | 210/252 |

* cited by examiner

*Primary Examiner*—John Kim
(74) *Attorney, Agent, or Firm*—Heslin Rothenberg Farley & Mesiti P.C.; Candice J. Clement, Esq.

(57) ABSTRACT

A filtration system and method for the filtration of a biological liquid are disclosed. The system and method may include a biological liquid collection assembly, a filtration assembly in communication with the collection assembly and a blood components preservative assembly in communication with the collection assembly. The preservative assembly includes a blood components preservative container and the preservative container may contain a blood components preservative solution and contains a measured quantity of a sterile gas. The preservative assembly is adapted to automatically transfer at least a portion of, respectively, the preservative solution, if present, and the gas to the collection assembly under a force of gravity once fluid flow communication is commenced between the preservative container and the collection assembly. Further, when the collection container contains at least a portion of the biological liquid and a transferred portion of the preservative solution, if present, and the gas, the collection container is adapted to automatically transfer at least a portion of, respectively, the biological liquid, the preservative solution, if present, and the gas to the filtration assembly under the force of gravity once fluid flow communication is commenced between the collection container and the filtration assembly.

16 Claims, 10 Drawing Sheets

GRAVITY DRIVEN LIQUID FILTRATION SYSTEM AND METHOD FOR FILTERING BIOLOGICAL LIQUID

FIELD OF THE INVENTION

This invention relates generally to biological liquid filtration systems and methods. More particularly, this invention relates to a non-vented gravity driven biological liquid filtration system and method usable to collect, filter and store biological liquids such as blood or blood components.

BACKGROUND OF THE INVENTION

Typically, blood filtration systems allow unfiltered liquid to remain within the filtration system after filtration has occurred. This remaining unfiltered liquid, referred to as a hold up volume, is often greater than the desired maximum amount. As discussed below, applicant has discovered that this will be particularly true in an in-line, closed system that does not use gas vents to aid in recovery of unfiltered liquid. Also, conventional blood filtration systems do not limit the interface of gas with biological liquid in the system to provide a more consistent and safe processed blood product, nor do they provide as simple and as automatic a system as the present invention.

Certain blood filtration devices are disclosed in the following patents or applications: U.S. Pat. No. 5,472,605, entitled "A Filtration Device Usable for Removal of Leukocytes and Other Blood Components" issued Dec. 5, 1995; U.S. Pat. No. 5,798,041, entitled "An In-Line Liquid Filtration Device Usable for Blood, Blood Products and the Like"; U.S. Pat. No. 6,010,633, entitled: "In-line Gravity Driven Liquid Filtration Device Usable to Filter Blood or Blood Products" issued Jan. 4, 2000; U.S. Ser. No. 09/260,967, entitled "System and Method of Filtering and Collecting Blood or Blood Products" filed Mar. 2, 1999, abandoned; and, U.S. Ser. No. 09/133,245, entitled "Improved Flow Distributor and Method for Use with a Filter Device" filed Aug. 13, 1998, abandoned, and these all are incorporated by reference and made a part of the disclosure herein. Filtration methods using these types of devices rely upon, at least in part, a vented system to maximize the recovery of blood or blood product upstream of the filter. Because of such a venting feature, at least in part, these prior art devices are unlike the present invention, although they are similar in other respects except as discussed hereafter.

Conventional teaching in the art of blood filtration suggests that such filtration systems can have only 5 ml or less of gas per bag in any bag of the blood collection systems, i.e., upon set up of the system. This is according to the 1997 ISO 3826 practice, which is industry practice prior to and at the time of applicant's invention. Additionally, conventional teaching in the art suggests that gas and blood interfacing in the system is not desirable due to potential damage to blood constituents, and the longer the time of interface the more likely that gas-borne contaminants may get into the blood. Finally, it is known that an increase in recovery of only 1–2% of the total biological liquid processed in a system (e.g., due to hold up volume) may make a large difference in the art. In fact, International Regulations require that a system have at least 85% recovery and typically 90% or above. Moreover, the recovery rate of 85% is required for 100% of the systems used.

In light of the foregoing, it may be desirable to obtain a liquid filtration system and method that enhance the recovery of biological liquids, especially in a non-vented biological liquid filtration system. Also, it may be desirable to operate any such system as automatically as possible to reduce the need for human intervention (e.g., eliminating squeezing of containers in the system when transferring container contents) and to cause liquid processing to occur merely under a force of gravity and/or atmospheric pressure or other natural environmental forces acting in or upon the system. Further, it may be desirable to limit the time and amount of exposure of gas in the system with the biological liquid being processed.

SUMMARY OF THE INVENTION

The shortcomings of the prior art may be alleviated and the aforementioned goals may be achieved by using a filtration system and method in accordance with one or more principles of the present invention. The filtration system and method of the present invention is useable when filtering blood or blood components to remove leukocytes, other blood components, cells, or chemical agents which may be used to treat the blood. Additionally, other uses may be made of the invention which fall within the scope of the claimed invention but which are not specifically described below.

In one aspect of the invention, there is provided a filtration system and method for the filtration of a biological liquid such as blood or blood components. The system includes a biological liquid collection assembly, a filtration assembly in communication with the biological liquid collection assembly and a blood components preservative assembly in communication with the biological liquid collection assembly. The blood components preservative assembly includes a blood components preservative container and the blood components preservative container may contain a blood components preservative solution and contains a measured quantity of a sterile gas. The blood components preservative assembly is adapted to automatically transfer at least a portion of, respectively, the blood components preservative solution, if present, and the sterile gas to the biological liquid collection assembly under a force of gravity once fluid flow communication is commenced between the blood components preservative container and the biological liquid collection assembly.

In another aspect of the invention there is provided a method for processing biological liquid in said filtration system. The method includes providing the biological liquid in the biological liquid collection container and automatically transferring at least a portion of, respectively, the blood components preservative solution, if present, and the measured quantity of the sterile gas into the biological liquid collection container under the force of gravity. Further, the method may include automatically transferring at least a portion of, respectively, the biological liquid, the blood components preservative solution, if present, and the sterile gas under the force of gravity to a biological liquid filter downstream of the biological liquid collection container and collecting the biological liquid and blood components preservative solution, if present, that have passed through the biological liquid filter into a biological liquid storage container.

Yet other aspects of the invention concern: a satellite bag assembly in communication with the biological liquid collection assembly; particular configurations for connecting various components of the system; and, particular attributes of certain components of the system, all which can enhance safe and efficient use of the system, as desired.

DESCRIPTION OF THE DRAWINGS

Other features and aspects of the invention will become more readily apparent upon reference to the following description when taken in conjunction with the accompanying drawings, which drawings illustrate embodiments of the invention.

DETAILED DESCRIPTION OF THE PREFERRED EMBODIMENTS

Figure 1:
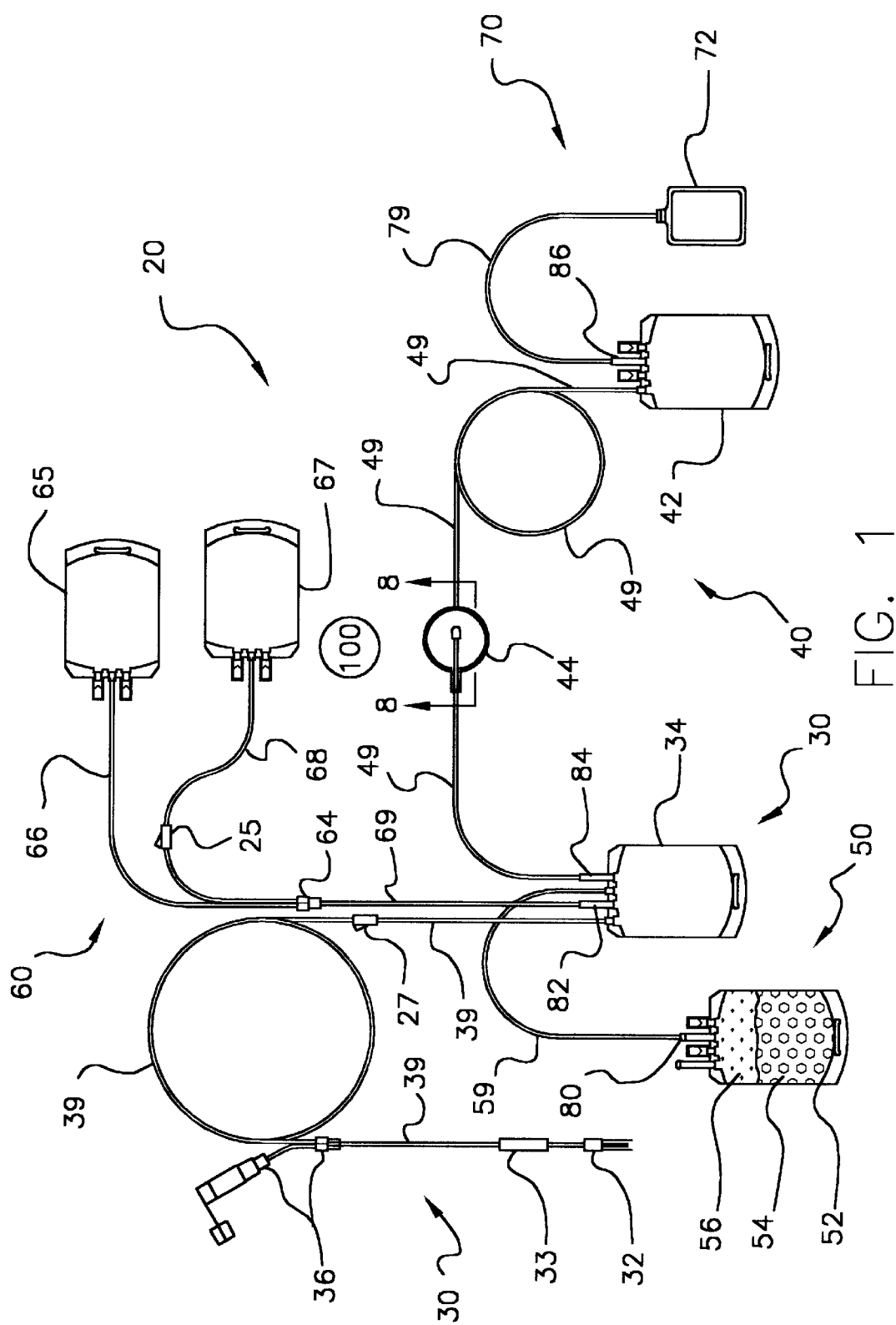
FIG. 1 is a schematic representation of a filtration system useable to collect, filter and store biological liquids such as blood or blood components in accordance with features of the present invention.
Figure 2:
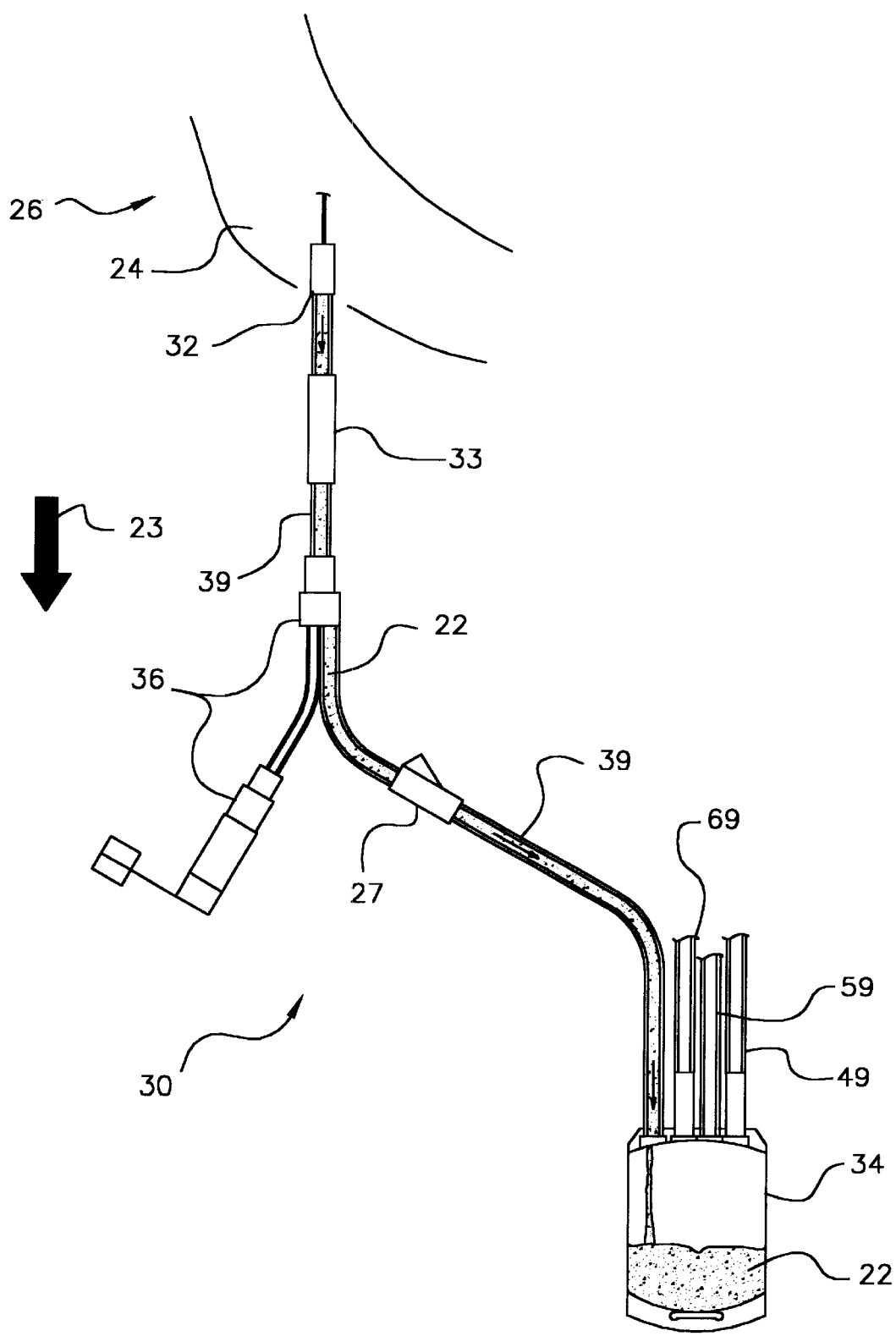
FIG. 2 is a schematic representation of a portion of the system seen in FIG. 1, e.g., a biological liquid collection assembly, and here also showing operation of the system.

Referring to the FIG., e.g., FIG. 1, there is seen an embodiment of the invention comprising a filtration system 20 for the filtration of a biological liquid 22 (e.g., FIG. 2). The system and method of the present invention may be used for the filtration of various liquids including biological liquids. However, they are particularly suited for the filtration of blood and/or blood components and thus will be described herein in reference to blood filtration for illustration purposes.

Preferably, filtration system 20 is a closed in-line filtration system. More preferably, system 20 is also a non-vented system. These preferred conditions are desirable, e.g., to enhance system performance and simplicity and to enhance system sterility. As used herein, the term "in-line" means a system with components pre-connected before use and the system as a whole in a sterile condition once pre-connected and then ready for use. Differently, the term "closed" means a system where an interior of the system (i.e., within the tubings, containers, filter and associated components) is in communication with an environment external to the system (i.e., the atmosphere 100 surrounding the system) only through a port or opening in the system which is covered by a sterile grade filter. Such a "closed" system which is vented is seen in U.S. Pat. No. 6,010,633, as well as other patents and applications cited previously which are incorporated herein by reference. Further, such a "closed" system which is not also "in-line", i.e., because conventional sterile docking connections are connected only after commencing use of the system, is seen in U.S. Pat. No. 5,128,048, entitled: "Systems and Methods for Removing Undesired Matter From Blood Cells" issued Jul. 7, 1992, which is incorporated herein by reference. Finally, as used herein, the term "non-vented" means that there are no ports or other openings in the system by which gas can communicate between an interior of the system (i.e., within the tubings, containers, filter and associated components during use of the system) and an environment external to the system (i.e., the atmosphere 100 surrounding the system).

Returning to FIG. 1, system 20 may include a biological liquid collection assembly 30, a filtration assembly 40 and a blood components preservative assembly 50, where both assemblies 40 and 50 are in communication with collection assembly 30. Also referring to FIG. 2, Collection assembly 30 may include a biological liquid collection device 32 adapted to communicate with a biological liquid source 24. Device 32 may be a conventional blood collection needle or cannula or other means for providing biological liquid to collection assembly 30. Device 32 may also include a needle guard 33 or similar mechanism. Liquid source 24 may be a living subject, such as a human donor 26 or other animal. Biological liquid may be collected directly from source 24 and into collection assembly 30, as in FIG. 2, by simple gravity transfer where the collection assembly 30 is maintained at a height below that of source 24. Alternatively, biological liquid may be collected from source 24 at a first time using a separate collection means and then at a later time collection device 32 of collection assembly 30 may be connected with the separate collection means, e.g., by conventional teaching in the art, and thereafter liquid can be directed into collection assembly 30, by gravity preferably.

Figure 3:
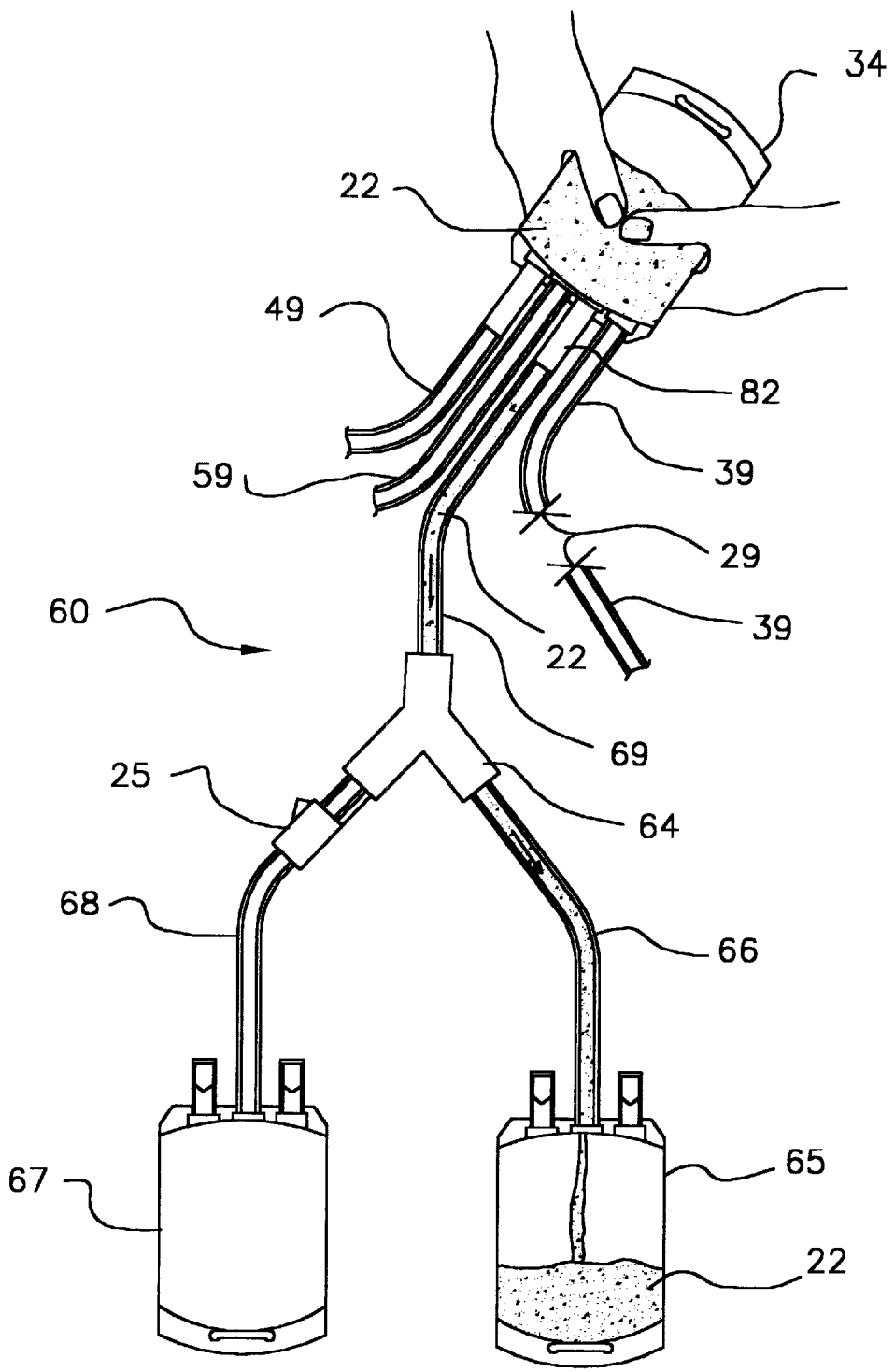
FIG. 3 is a schematic representation of a portion of the system seen in FIG. 1, e.g., a satellite bag assembly, and here also showing operation of the system.

Collection assembly 30 may include a biological liquid collection container 34. Collection container 34 is, preferably, in direct communication with collection device 32 independent of at least filtration assembly 40 and/or preservative assembly 50. In this way, this portion of system 20 can be easily removed when it is no longer needed without compromising any other portions of system 20. Collection container 34 is preferably connected with collection device 32 via a flexible tubing 39 of a type conventionally used in the medical arts, e.g., for biological liquid or blood—collection or filtration. Tubing 39 can be sealed and cut in a conventional way (e.g.,, as in FIG. 3 represented by symbol 29 where the opposing separated tubing is not shown) to separate collection container 34 from collection device 32 along with a majority of tubing 39 therebetween, when desired. A conventional type clamp 27 (e.g., roller clamp, hemostat, etc.) may be placed along tubing 39 to assist in collection of biological liquid, either when said liquid is collected directly or indirectly as discussed above. Also, conventional sampling site means 36 may be employed, as desired, in the collection assembly tubing 39.

Blood components preservative assembly 50 is preferably in communication with collection assembly 30. Preservative assembly 50 includes a blood components preservative container 52 which may contain a blood components preservative solution 54 and contains a measured quantity of a sterile gas 56. Preservative solution 54 may be any conventional blood or blood components preservative solution, e.g., AS-1, AS-3, AS-5 or SAGM. Sterile gas 56 may be any conventional sterile gas, e.g., sterile air. Preferably, gas 56 it will be of a quantity dependent on system requirements but generally in an amount of about 20 ml to about 50 ml, provided this is enough to drain residual liquid 22 upstream of filter 44, as described further below. Preservative container 52 may be connected with collection container 34 via a flexible tubing 59 of the same type as tubing 39.

A satellite bag assembly 60 is preferably in communication with collection assembly 30. Also preferably, satellite bag assembly 60 is downstream of collection assembly 30. Satellite bag assembly 60 may include one or more satellite bag containers 65 and 67. However, any number of satellite bags equal to the number of desired blood components to be separated from the blood may be used, e.g., 1, 2, 3, or more. Bag containers 65 and 67 may share a common path in communication with collection assembly 30. For example, bag containers 65 and 67 may be connected with collection container 34 via a common flexible tubing 69 of the same type as tubing 39. Then, tubing 69 may be connected, via a conventional y-connector 64, to tubings 66 and 68 which are also of the same type as tubing 39 and which tubings 66 and 68, respectively, connect with bag containers 65 and 67. A clamp 25, similar to clamp 27, may be placed along tubing 68 to assist in transfer of liquid 22 from collection container 34 or of liquid 22 between satellite bag containers 65 and 67. In one aspect, preferably satellite bag assembly 60 is in direct communication with collection assembly 30 independent of at least one of the members from the group consisting of filtration assembly 40 and preservative assembly 50. In this way, this portion of system 20 can be easily removed when it is no longer needed without compromising any other portions of system 20.

In one aspect, preservative assembly 50 is adapted to automatically transfer at least a portion of preservative solution 54, if present, and sterile gas 56 to collection assembly 30 under a force of gravity in a downward direction 23, i.e., by suspending preservative container 52 above collection container 34, as in FIG. 4, once fluid flow communication is commenced between preservative container 52 and collection container 34, as discussed below. Further, preferably, the force of gravity also includes atmospheric pressure, i.e., as exerted on the outside of the walls of preservative container 52. Still, more preferably, the force which causes preservative solution 54 and sterile gas 56 to transfer comprises substantially only gravity and atmospheric pressure. In these preferred and more preferred ways, system complexities are further minimized and automatic features are enhanced, thus leading to a more efficient, safe and user friendly system 20. Additionally, the applicant has discovered that by putting the measured amount of sterile gas 56 in preservative container 52, one can maximize the recovery of not only biological liquid later, as in FIGS. 5 and 5a, but also the recovery of preservative solution 54, if present, when it is first mixed with the biological liquid, as in FIGS. 4 and 4a.

Filtration assembly 40 is preferably in communication with collection assembly 30. Filtration assembly 40 may include a biological liquid storage container 42 downstream of collection assembly 30. Filtration assembly 40 may further include a biological liquid filter 44 disposed between storage container 42 and collection assembly 30. For example, filter 44 may be connected upstream thereof with collection container 34 via a flexible tubing 49 of the same type as tubing 39. Further, filter 44 may be connected downstream thereof with storage container 42 via flexible tubing 49 also. In one aspect, preferably biological liquid communicates with storage container 42 via a single communication path passing through filter 44. In this way, needless by-pass lines are avoided and system complexity and sterility are better served. In another aspect, preferably filtration assembly 40 and preservative assembly 50 are each in direct communication with collection assembly 30 independent of each other. In this way, these portions of system 20, respectively, can be easily removed when no longer needed without compromising any other portions of system 20.

Figure 5:
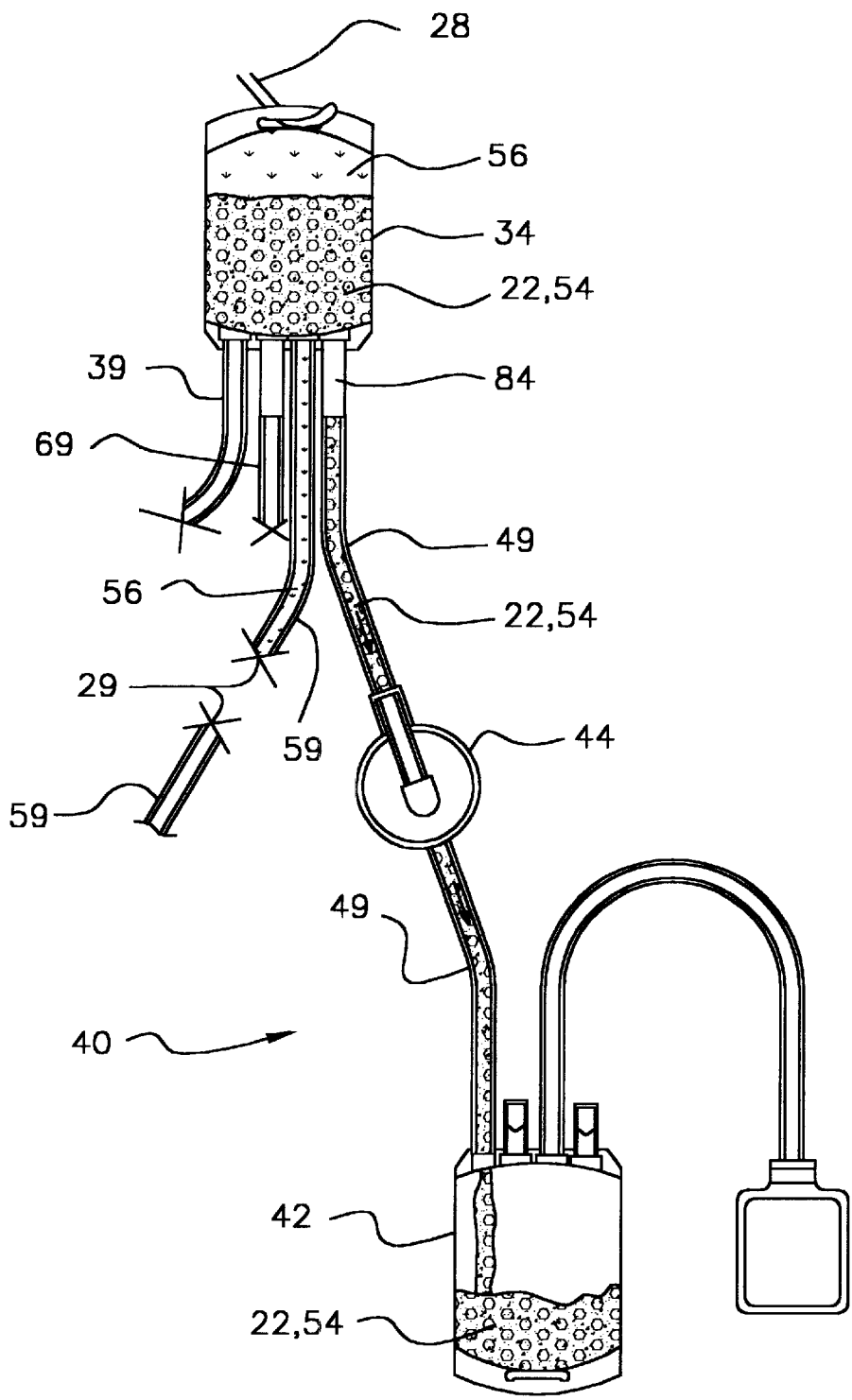
FIG. 5 is a schematic representation of a portion of the system seen in FIG. 1, e.g., a filtration assembly, and here also showing operation of the system.

In one aspect, when collection container 34 contains at least a portion of liquid 22 and a transferred portion of preservative solution 54 and sterile gas 56, collection container 34 is adapted to automatically transfer at least a portion of liquid 22, preservative solution 54 and sterile gas 56 to filtration assembly 40 under a force of gravity, i.e., by suspending collection container 34 above filtration assembly 40 as in FIG. 5, once fluid flow communication is commenced between collection container 34 and filtration assembly 40. Further, preferably, the force of gravity also includes atmospheric pressure, i.e., as exerted on the outside of the walls of collection container 34. Still, more preferably, the force which causes liquid 22, preservative solution 54 and sterile gas 56 to transfer comprises substantially only gravity and atmospheric pressure. In these preferred and more preferred ways, system complexities are further minimized and automatic features are enhanced, thus leading to a more efficient, safe and user friendly system 20. For example, applicant made a discovery in arriving at the present invention. This discovery was that, contrary to the conventional teaching against putting gas into such a system, in the present invention the problem of gas 56 and liquid 22 interfacing is reduced because gas 56 and liquid 22 interface only after certain liquid components are removed, as in FIG. 3 (i.e., after removal of plasma and/or plasma and platelets, etc.). Then, with the present invention the interface is limited to the time it takes liquid 22 to pass through filter 44 because after all liquid 22 passes through filter 44 gas 56 is trapped upstream of filter 44 by the liquid wetted filter medium in filter 44, described further below.

Filtration assembly 40 may also include an air collection assembly 70. Collection assembly 70 may include an air collection assembly container 72 which is connected with storage container 42 via a flexible tubing 79 of the same type as tubing 39. Storage container 42 is adapted to be squeezed by a user, as in FIG. 6, and thereby transfer residual gas from storage container 42 into air collection assembly container 72. Also, preferably, a portion of filtered liquid 22, 54 may be transferred into tubing 79, as in FIG. 7, and remain there for later use (e.g., for sampling, quality control, etc., as described in U.S. Ser. No. 09/260,967, abandoned).

As part of tubings 49, 59, 69 and 79 are included flow control devices 84, 80, 82 and 86, respectively. Although a clamp, like that of clamp 27, could be used in place of the flow control devices, as would be known in the art, the flow control devices are preferable. The flow control devices could be any conventional type device that normally blocks the flow of liquid through the associated tubing. Then, through user manipulation of the device, such as bending a frangible cannula, this breaks open the interior of the associated tubing to allow liquid to flow through the device and within the tubing. The use of the flow control devices is employed as explained below.

The components of system 20 are generally made of conventional materials, and intended to be interchangeable with related conventional components, except as noted herein. For example, all tubings 39, 49, 59, etc. could be made of any medical grade plastic-type tubing or the like that is, preferably, flexible and semi-rigid. Containers 65, 67, 42 and 72 could be made of any medical grade container material, such as a plastic-type or the like material, that is, preferably, flexible and not rigid much at all and adapted for longer term storage of biological liquid such as blood or blood components. Preferably, all of the tubings and containers of system 20 are either formed integrally with each other or are connected in a secure and sterile manner, using conventional means and methods. A presently available product that contains at least one tubing, container, flow control device and clamp, each meeting requirements of the invention discussed herein above, is available from HemaSure, Inc of Marlborough, Mass. 01752 under the name r/LS™ blood filtration system.

Referring to containers 52 and 34, these are similar to the other containers of system 20 but preferably comprise containers of a material that is used for such containers in a product sold by the Korean Green Cross under the name Blood Collection Set, which is available from Green Cross Medical Corp. Seoul, Korea. In this regard, it is desirable to transfer sterile gas 56 from preservative container 52 to collection container 34 without having to squeeze preservative container 52. Accordingly, a container material that will drain automatically under merely the forces of gravity and/or atmospheric pressure is desired for use in the invention and is preferably made of a material of sufficient mass and flexibility to collapse under its own weight during processing. In this way, a user does not have to squeeze the container to cause preservative solution 54, if present, and sterile gas 56 (i.e., and then these two and biological liquid 22) to drain from one container to another during processing because system 20 would operate under merely environmental forces. To date, the product made by the Green Cross of Korea is believed to meet these requirements.

Figure 8:
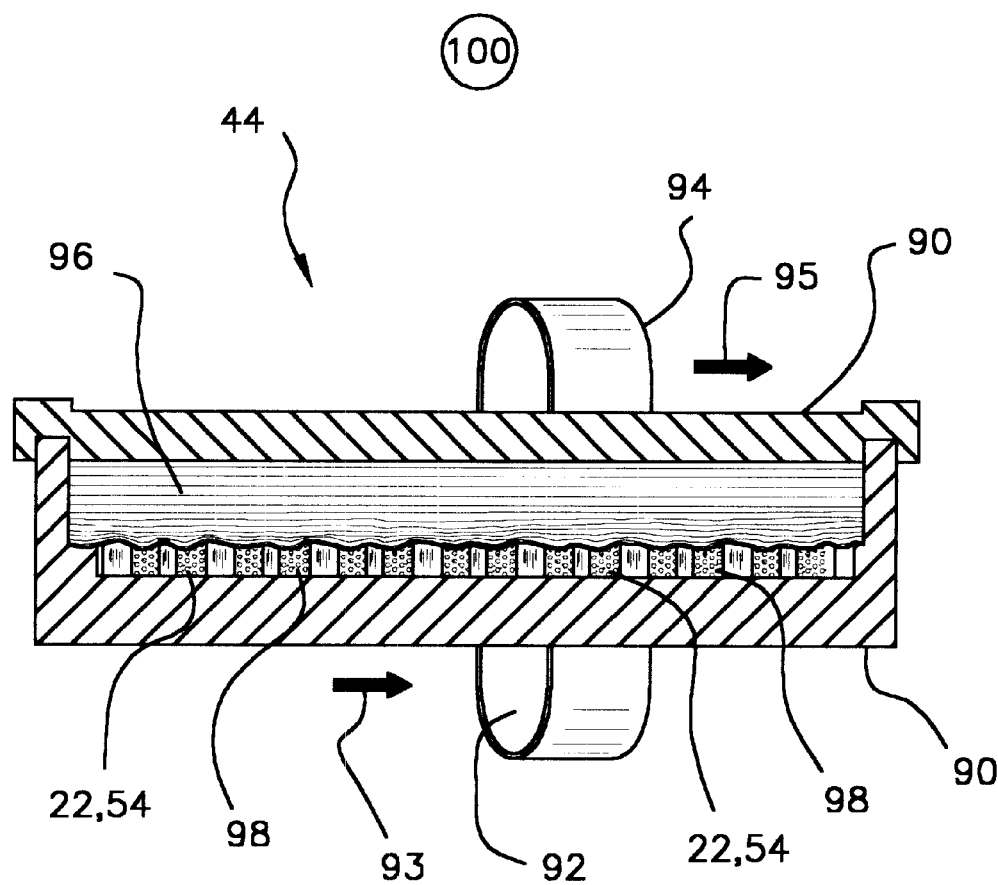
FIG. 8 is a cross-sectional view of a filter, taken through the line 8—8 of FIG. 1, according to preferred features of the invention.

Filter 44 could include most any conventional filter used for filtering biological liquid and is preferably adapted to filter blood or blood components (e.g., platelets, plasma, red blood cells, white blood cells, or any combination of these and at least concentrated blood cells). Referring to FIG. 8, filter 44 may comprise a housing 90 (e.g., made of polycarbonate or similar material) with an inlet 92 to receive unfiltered liquid 93 and an outlet 94 to exit filtered liquid 95. A filter medium 96 can be disposed within the housing between the inlet and the outlet to filter certain constituents out of the liquid. Other than the inlet and the outlet, preferably filter 44 has no port or pathway on or in the filter housing for enabling communication between the interior of the filter housing and an environment 100 external to the filter housing, i.e., the atmosphere outside of filter 44. Filter 44 may filter any of a variety of constituents out of the liquid being flowed through it, but preferably it will reduce a quantity of leukocytes (i.e., white blood cells) or a biological liquid chemical agent (e.g., methylene blue) in the biological liquid during filtration of same. An example of such a filter 44 as contemplated here is found in U.S. Pat. Nos. 5,798,041, 6,010,633, U.S. Ser. No. 09/260,967, abandoned, U.S. Ser. No. 09/133,245, abandoned, or generally available from HemaSure, Inc of Marlborough, Mass. 01752 under the name r/LS™, except that the filter of the r/LS™ system and the just-referenced patents and applications has a vent on the filter housing. Thus, if the vent of the r/LS™ system and the just-referenced patents and applications is removed or permanently closed, as could be done by one of ordinary skill in the art based on the teaching here, then such a filter 44 as desired for the present invention would be made. A further example of an acceptable filter medium for filter 44 can be found in U.S. Ser. No.: 09/264,276 entitled Leukocyte Reduction Filtration Media, abandoned, which is incorporated fully herein by reference.

Another aspect of the invention relates to a method for processing biological liquid, e.g., liquid 22, in filtration system 20. A preferred method may include the following steps, in the following order, although other steps and orders may be desirable under certain conditions. Referring to the figures, e.g., starting with FIG. 1, there is seen system 20 with desired components in an in-line closed ready to use configuration. Going to FIG. 2, biological liquid 22 is collected, e.g., via biological liquid collection device 32, from source 24 and into biological liquid collection container 34 by simple gravity transfer using conventional blood collection techniques. Alternatively, liquid may be collected from source 24 at a first time using a separate collection container and then at a later time collection device 32 may be connected with the separate collection container already filled with biological liquid. Then, liquid can be transferred from the separate collection container to collection container 34 using gravity and conventional blood collection techniques. During liquid collection, conventional sampling can be conducted via sampling site means 36. It is noted that components of system 20 (i.e., when still remaining connected thereto) seen in FIGS. 2 and 3–5 hang down in a vertical orientation from the uppermost component and are shown with accentuated curves or bends in the tubings only for illustration purposes here.

Referring now also to FIG. 3, once the liquid is collected into collection container 34, tubing 39 is sealed and separated at 29, e.g., by cutting or snapping apart the seal by conventional means such as a heat seal and scissors cut. In this way, this portion of system 20 can be easily removed without compromising the sterility of any other portions of system 20. Then, the biological liquid can be separated into desired blood components (e.g., plasma concentrate, plasma and platelet concentrate, blood cell concentrate, etc.), by conventional separation techniques such as centrifugation. One or more of the separated components can be transferred into satellite bag assembly 60. In this regard, flow control device 82 must first be opened and then transfer can occur by conventional expressing techniques to force out the separated components(s) into satellite bag containers 65 or 67 if clamp 25 is closed, or alternatively, into both containers 65 and 67 if clamp 25 is open.

Figure 4:
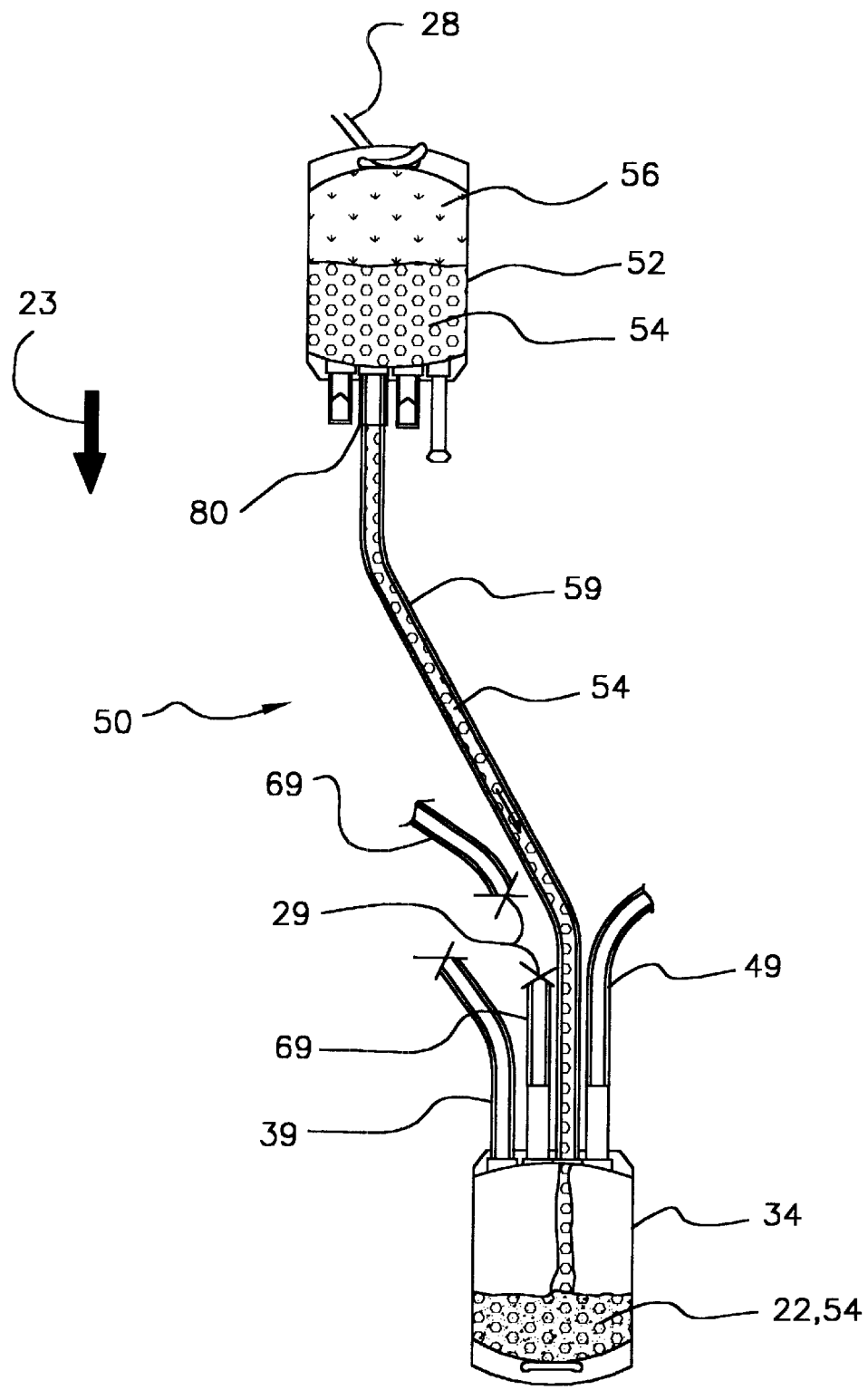
FIG. 4 is a schematic representation of a portion of the system seen in FIG. 1, e.g., a blood components preservative assembly, and here also showing operation of the system.

Now referring to FIGS. 3 and 4, once the separated blood component(s) are transferred out of collection container 34 thus leaving only remaining blood component(s) in container 34, tubing 69 is sealed and separated at 29 in a manner similar to that of tubing 39 previously. Because bag containers 65 and 67 may share a common path below the y-connector 64, one or more blood component may be further separated in satellite bag container 65 or 67, using conventional separation techniques such a centrifugation. Then, the further separated component may be transferred to the other satellite bag container in a manner similar to that for transfer of the blood component(s) from collection container 34, e.g., by conventional expressing techniques. In this regard, clamp 25 will be opened as necessary. Once transfer between containers 65 and 67 is complete, tubings 66 and 68 may be sealed and separated above their respective containers in a manner similar to that of tubing 39 previously. The contents of containers 65 and 67 can then be prepared for later use by conventional blood component preparation techniques.

Referring to FIG. 4, blood components preservative container 52, which contains blood components preservative solution 54 and a measured quantity of sterile gas 56, can then be suspended from a conventional hook 28, which is secured to a conventional stand or other structure. Next, flow control device 80 is opened and then preservative solution 54 begins to drain into collection container 34 under a force of gravity, i.e., automatically without the need for any user assistance once flow control device 80 is opened. Also referring to FIG. 4a, as preservative solution 54 is completely drained from preservative container 52, sterile gas 56 begins to also drain from preservative container 52 by chasing the remaining preservative solution 54 through tubing 59 and into collection container 34. As described above as applicant's discovery, if gas 56 is not used to chase preservative solution 54, then a residual amount of solution 54 would remain in the bottom of preservative container 52 and then also in tubing 59 connected between this container and collection container 34. Thus, one feature of applicant's invention is to be able to recover such residual preservative solution 54 that has been traditionally lost in prior art systems. As concerns the cause of the transfer of gas 56 to collection container 34, as best understood by applicant and part of his discovery as explained above, it is the force of gravity and atmospheric pressure, i.e., as exerted on the outside of the walls of preservative container 52, which causes automatic transfer of gas 56 without the need for user intervention such as squeezing of preservative container 52. Thus, preferably, the force which causes preservative solution 54 and sterile gas 56 to transfer comprises substantially only gravity and atmospheric pressure, as described above, in order to obtain more system efficiency through less user intervention.

Figure 4A:
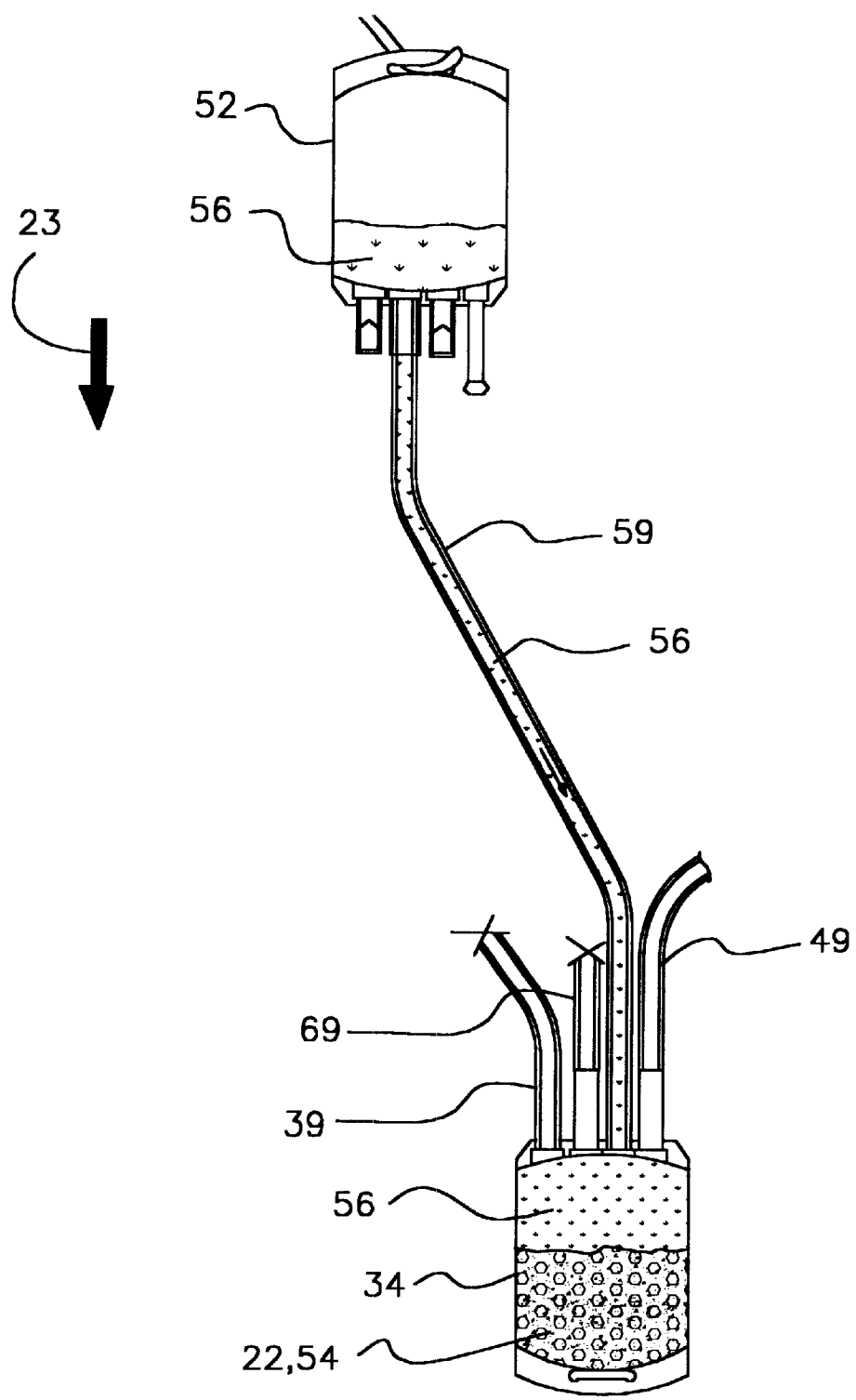
FIG. 4a is a schematic representation of the portion of the system seen in FIG. 4, now one step later.

Referring to FIGS. 4a and 5, once preservative solution 54 and a measured quantity of sterile gas 56 are transferred to collection container 34, tubing 59 is sealed and separated at 29 in a manner similar to that of tubing 39 previously. Next, preservative solution 54 is thoroughly mixed with the remaining blood component(s) in collection container 34 by conventional techniques.

Referring to FIG. 5, collection container 34, with sterile gas 56 and preservative solution 54 mixed with the remaining blood component(s) therein, can then be suspended from hook 28. Next, flow control device 84 is opened and then preservative solution 54 mixed with the remaining blood component(s) begins to flow through tubing 49, then filter 44 and then tubing 49 and into biological liquid storage container 42, all under a force of gravity, i.e., automatically without the need for any user assistance once flow control device 84 is opened. As preservative solution 54 mixed with the remaining blood component(s) is completely drained from collection container 34, sterile gas 56 begins to also drain from collection container 34 by chasing the remaining preservative solution 54 mixed with the remaining blood component(s) through tubing 49 and into filter 44. Filter 44, when comprising a structure as preferred here, has a chamber 98 within housing 90 and upstream of filter medium 96 (see FIG. 8). Thus, sterile gas 56 will continue to chase the remaining preservative solution 54 mixed with the remaining blood component(s) into the upstream chamber 98 of the filter housing and cause the upstream chamber to drain of substantially all remaining preservative solution 54 mixed with the remaining blood component(s).

Now, the filter medium as preferred here may be hydrophilic. Such a hydrophilic medium would allow the passage of gas therethrough until wetted by liquid and thereafter only allow the passage of liquid and prevent the passage of gas. Thus, and also referring to FIG. 5a, once substantially all remaining preservative solution 54 mixed with the remaining blood component(s) drains from upstream chamber 98, only sterile gas 56 fills the upstream chamber and the flow of liquid through system 20 stops since gas 56 cannot flow through filter medium 96 to continue chasing the liquid 22, 54 downstream of filter medium 96. As concerns the cause of the transfer of gas 56 to filter 44, as best understood by applicant and part of his discovery as explained above, it is similar to that for preservative container 52. Thus, preferably, the force which causes preservative solution 54 mixed with the remaining blood component(s) and sterile gas 56 to transfer comprises substantially only gravity and atmospheric pressure, as described above, in order to obtain more system efficiency through less user intervention. Also, preferably, it should now be understood that sterile gas 56 be of a quantity, dependent on system requirements but generally in an amount of about 20 ml to about 50 ml, sufficient to, first, drain preservative solution 54 from preservative container 52 and then, second, drain preservative solution 54 mixed with the remaining blood component(s) from collection container 34 and chamber 98 of filter 44.

As described above as applicant's discovery, if gas 56 is not used to chase preservative solution 54 mixed with the remaining blood component(s), then a residual amount of preservative solution 54 mixed with the remaining blood component(s) would remain in the bottom of collection container 34, in tubing 49 connected between this container and in upstream chamber 98 of filter 44. Thus, one feature of applicant's invention is to be able to recover such residual preservative solution 54 mixed with the remaining blood component(s) that has been traditionally lost in prior art systems, similar to that for preservative container 52 described previously. That is, then, with applicant's invention the only significant loss of remaining preservative solution 54 mixed with the remaining blood component(s) is found in the liquid soaked filter medium 96, in a chamber (if one exists) within the filter housing downstream of filter medium 96 and in tubing 49 between filter 44 and storage container 42. However, even a majority of liquid remaining in the portion of tubing 49 downstream of filter 44 can be recovered into storage container 42 by conventional techniques such as stripping tubing 49 between filter 44 and container 42. Alternatively, though, liquid remaining in the downstream portion of tubing 49 can be left there for later use, as desired, such as for quality control testing, sampling or the like.

Figure 5A:
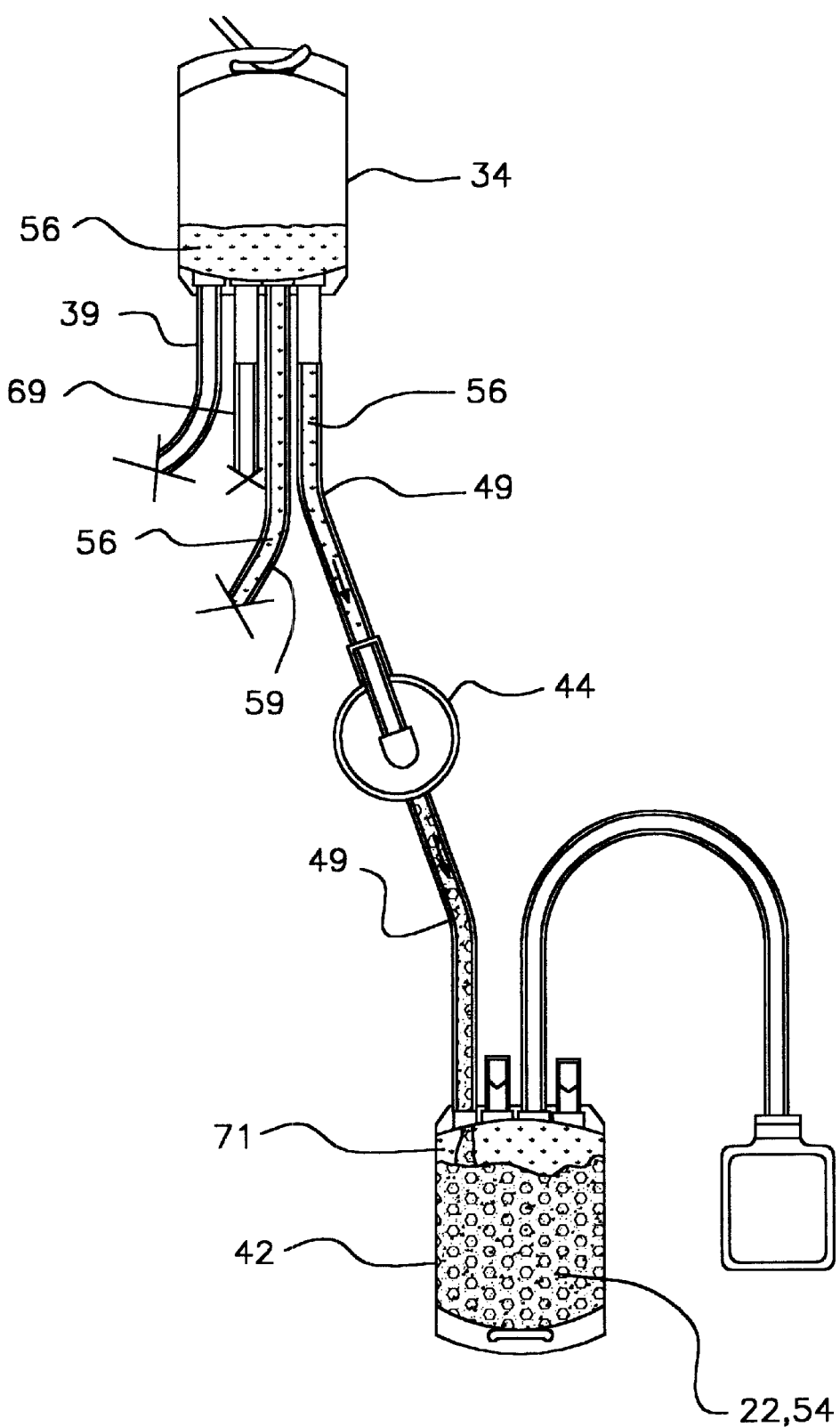
FIG. 5a is a schematic representation of the portion of the system seen in FIG. 5, now one step later.
Figure 6:
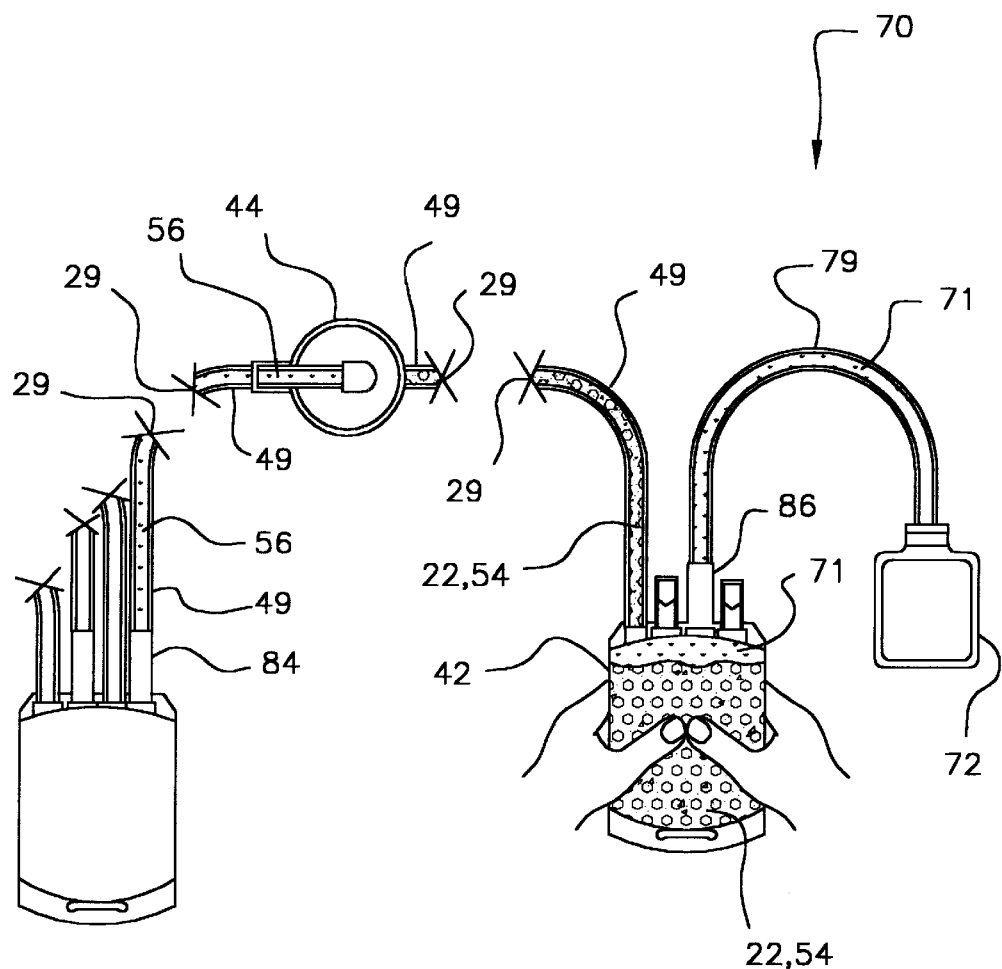
FIG. 6 is a schematic representation of a portion of the system seen in FIGS. 1 and 5, e.g., an air collection assembly, and here also showing operation of the system.

Referring to FIGS. 5a and 6, once filtration of liquid in system 20 has stopped, and tubing 49 is stripped or not as desired, tubing 49 is sealed and separated at 29 in a manner similar to that of tubing 39 previously. If tubing 49 is not stripped (FIG. 7), then it may be sealed but not separated at 31, to create individual pockets of filtered liquid for said later use. Next, the filtered preservative solution 54 and the remaining blood component(s) in storage container 42 can be further mixed by conventional techniques.

Figure 7:
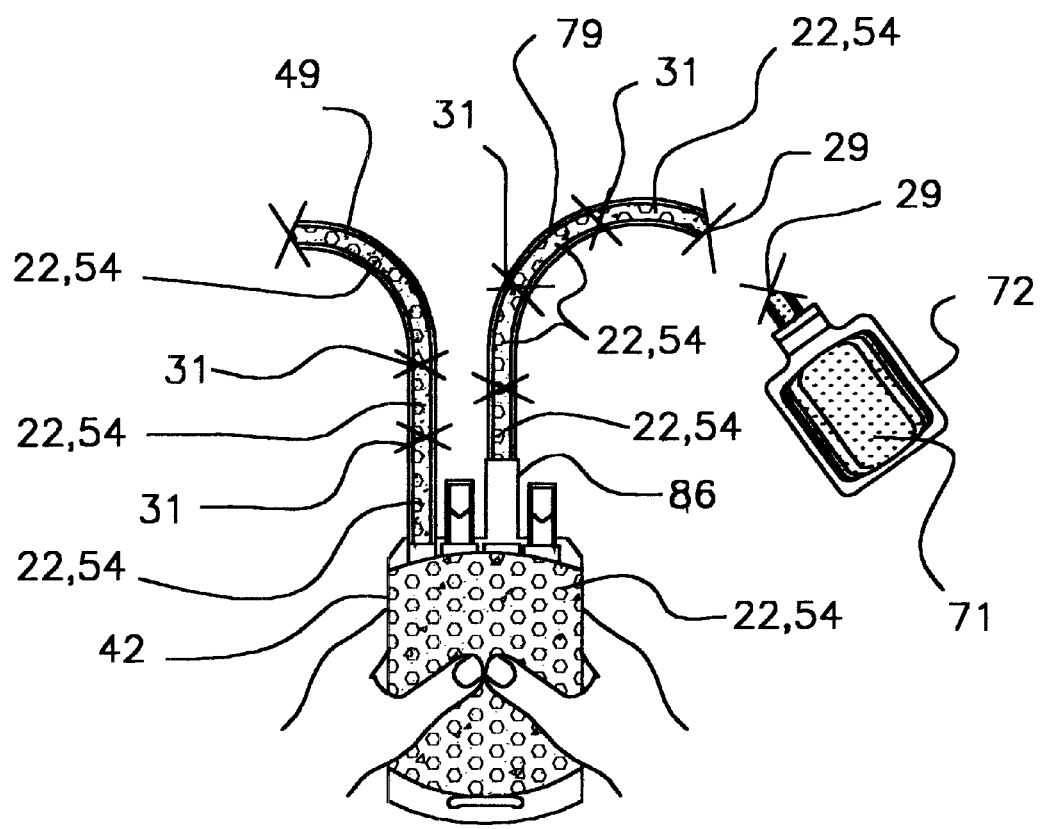
FIG. 7 is a schematic representation of a portion of the system seen in FIGS. 1, 5 and 6, and here also showing operation of the system.

Referring to FIG. 6, residual gas 71 present in system 20 (residual gas 71 is other than sterile gas 56 and comprises the residual air left in the system after sterilization and chased from the system by liquid flowing in the system, e.g. air in the filtration media is chased down stream by the first liquid flowing there through and is chased into tubing 49 and then storage container 42 by the liquid), which is a problem addressed by applicant's corporation in U.S. Ser. No. 09/260,967, abandoned, can be transferred to air collection assembly container 72, by conventional techniques such as expressing described earlier. First, flow control device 86 is opened and then residual gas 71 can be expressed into air collection assembly container 72. Now, referring also to FIG. 7, a portion of filtered liquid 22, 54 may next be transferred into tubing 79, also by expressing, behind residual gas 71. Such transferred portion of liquid 22, 54 can remain in tubing 79 for later use (e.g., for sampling, quality control testing, etc., as described in U.S. Ser. No. 09/260,967, abandoned). Tubing 79 can then be sealed and separated at 29 in a manner similar to that of tubing 39 previously. Tubing 79 may be further sealed but not separated at 31, into segments containing filtered liquid 22, 54, for said later use. As seen in FIG. 7, storage container 42 and remaining portions of tubings 49 and 79, and the contents therein, can then be prepared for long-term storage, later use, both or the like, using conventional techniques. Finally, any portions of system 20 not specifically desired for some type of later use can then be disposed of as desired.

As various possible embodiments may be made in the above invention for use for different purposes and as various changes might be made in the embodiments above set forth, it is understood that all of the above matters here set forth or shown in the accompanying drawings are to be interpreted as illustrative and not in a limiting sense. It will be further apparent to one of ordinary skill in the art that said various modifications may be made to the embodiments without departing from the scope of the invention as defined in the following claims.

What is claimed is:

1. A method for processing a biological liquid in an in-line filtration system, the method comprising the steps of:

providing the biological liquid in a biological liquid collection container;

providing a measured quantity of a sterile gas in a second container, the measured quantity being greater than 5 mL and the second container being in fluid communication with the biological liquid collection container;

automatically transferring at least a portion of the measured quantity of sterile gas into the biological liquid collection container under a force of gravity;

automatically transferring the biological liquid, followed by the measured quantity of sterile gas, to a biological liquid filter downstream of the biological liquid collection container, under the force of gravity, wherein the biological liquid passes through the filter and the sterile gas is retained upstream of the filter; and collecting the filtered biological liquid in a biological liquid storage container.

2. The method of claim 1, wherein the measured quantity of a sterile gas is between about 20 mL and 50 mL.

3. The method of claim 1, wherein the second container further contains a volume of a blood components preservative solution, and wherein the blood components preservative solution is automatically transferred from the second container into the biological liquid collection container under the force of gravity prior to the automatic transfer of the sterile gas.

4. The method of claim 3, wherein the blood components preservative solution is automatically transferred with the biological liquid to and through the biological liquid filter and collected with the filtered biological liquid in a biological liquid storage container.

5. The method of claim 1, wherein the force includes atmospheric pressure.

6. The method of claim 4, wherein the force includes atmospheric pressure.

7. The method of claim 5, wherein the force comprises substantially only gravity and atmospheric pressure.

8. The method of claim 6, wherein the force comprises substantially only gravity and atmospheric pressure.

9. The method of claim 1, wherein providing includes collecting the biological liquid from a donor.

10. The method of claim 1, further comprising the steps of:

separating at least one component from the biological liquid in the biological liquid collection container; and transferring the at least one component to at least one satellite bag container the satellite bag container being in fluid communication with the biological liquid collection container.

11. The method of claim 10, wherein transferring the at least one component to the at least one satellite bag occurs before automatically transferring the sterile gas into the biological liquid collection container.

12. The method of claim 1, wherein automatically transferring the biological liquid to the biological liquid filter and collecting the filtered biological liquid comprises passing the biological liquid through a single communication path from the biological liquid collection container, through the biological liquid filter, into the biological liquid storage container.

13. The method of claim 4, further comprising separating one or both of the biological liquid collection container and the biological liquid storage container from the biological liquid filter after collecting the filtered the biological liquid and blood components preservative solution in the biological liquid storage container.

14. The method of claim 1, wherein passing the biological liquid through the biological liquid filter removes at least one member from a group consisting of a biological liquid component and a biological liquid chemical agent.

15. The method of claim 14, wherein passing the biological liquid through the biological liquid filter removes leukocytes from the biological liquid.

16. The method of claim 14, further comprising preparing the filtered biological liquid and the blood components preservative solution in the biological liquid storage container for later use, long-term storage or both.

* * * * *